United States Patent [19]

Vinnars et al.

[11] Patent Number: 5,646,187
[45] Date of Patent: Jul. 8, 1997

[54] USE OF ALPHA-KETOGLUTARATE

[75] Inventors: Erik Vinnars, Sigtuna; Jan Wernerman, Stockholm, both of Sweden

[73] Assignee: AB Erik Vinnars, Sigtuna, Sweden

[21] Appl. No.: 451,262

[22] Filed: May 26, 1995

Related U.S. Application Data

[63] Continuation of Ser. No. 175,403, filed as PCT/SE93/00426, May 14, 1993 published as WO93/23027, Nov. 25, 1993, abandoned.

[30] Foreign Application Priority Data

May 20, 1992 [SE] Sweden ................................. 9201584

[51] Int. Cl.$^6$ .................. A01N 37/18; A61K 31/195; A61K 31/04; A61K 31/40
[52] U.S. Cl. .................. 514/557; 514/561; 426/74; 426/271; 426/656; 426/658
[58] Field of Search ................................. 514/557, 561

[56] References Cited

FOREIGN PATENT DOCUMENTS

| | | |
|---|---|---|
| 25 30 246 | 7/1975 | Germany . |
| WO8200411 | 2/1982 | WIPO . |
| WO8303969 | 11/1983 | WIPO . |
| WO87/03806 | 7/1987 | WIPO . |
| WO89/03688 | 5/1989 | WIPO . |

OTHER PUBLICATIONS

Vinnars CA.112:11918 n 2nd Derwent Abstract WO/PCT 8903688 (May 5, 1989)("Post–traumatic patients").
Kihlberg et al C.A.117:137674B of WO/PCT 92 09277 (Jun. 11, 1992) (glutamine).
Veech Derwent Abstract of WO/PCT 87 03806 (Jul. 2, 1987) (parenteral nutrition) GA.109:116049w.
Univ Jefferson Thomas Derwent Abstract of U.S. 4981641 (Jan. 1, 1991) Osterholm GA. 115:35751r (1991).
Ashmead Derwent Abstract of WO/PCT 2nd U.S. 5292538 (to Jul. 22, 1992).
Schlienger et al GA. 91:1684130 (1977).
Cynober et al GA. 106:49069 A (1986).
Vavbourdoll et al CA 109:91682g (1988).
Wernerman et al C.A. 111:172866p (1989).
Rothetal GA. 115:105389e (1991).
Ljungvist C.A. 116:76382k (1991).
Vinnars, et al., Metabolic Effects of Four Intravenous Nutritional Regimens in Patients Undergoing Elective Surgery II. – Muscle Amino Acids and Energy–Rich Phosphates, Clinical Nutrition (1983), vol. 2, pp. 3–11.
Vinnars, et al., Influence of the Postoperative State on the Intracellular Free Amino Acids in Human Muscle Tissue, Annals of Surgery (1975), vol. 182, No. 6, pp. 665–671 and 2486–2501.
Jepson, et al., Relationship between glutamine concentration and protein synthesis in rat skeletal muscle, Am. J. Phys. (1988), vol. 255, pp. 166–172.

Roth, et al., Metabolic Disorders in Severe Abdominal Sepsis: Glutmine Deficiency in Skeletal MUscel, Clinical Nutrition (1982), vol. 1, pp. 25–41.
Leander, et al., Nitrogen Sparing Effect of Ornicetil® in the Immediate Postoperative State Clinical Biochemistry and Nitrogen Balance, Clinical Nutrition (1985), vol. 4, pp. 43–51.
Wernerman, et al., Glutamine and Ornithine–α–Ketoglutarate but Not Branched–Chain Amino Acids Reduce the Loss of Muscle Glutamine After Surgical Trauma, Metabolism (1989), vol. 38, No. 8, pp. 63–66.
Jeevanandam et al., Substrate and hormonal changes due to dietary supplementation with ornithine alpha ketoglutarate (OKG) in critically ill trauma victims, Clinical Nutrition, vol. 11, Special Supplement, (1992). pp. 26, 14th Congress of the European Society of Parenteral and Enteral Nutrition, Vienna (Austria).
Hammarqvist et al., Addition of Glutamine to Total Parenteral Nutrition After Elective Abdominal Surgery Spares Free Glutamine in Muscle, Counteracts the Fall in Muscle Protein Synthesis, and Improves Nitrogen Balance, Ann Surg. (1989), pp. 455–461.
Roth et al., Amino Acid Concentrations in Plasma and Skeletal Muscle of Patients with Acute Hemorrhagic Necrotizing Pancreatitis, Clin. Chem., vol. 31, No. 8 (1985), pp. 1305–1309.
Karner et al., Alanyl–Glutamine Infusions to Patients with Acute Pancreatitis, Clin. Nutr., vol. 9, (1990), pp. 43–44.

*Primary Examiner*—Shep K. Rose
*Attorney, Agent, or Firm*—Pollock, Vande Sande & Priddy

[57] ABSTRACT

The invention relates to the use of alpha-ketoglutarate or analogues thereof in the preparation of a medicament for treatment of critically ill patients for improving protein synthesis capacity, maintaining energy level, preserving the lean body mass and for improving the glutamine content in skeletal muscle. The medicament contains preferably alpha-ketoglutarate in such an amount, so that it provides more than 0.25 g/kg body weight/day of alpha-ketoglutarate, when administered to the patient. The medicament can also comprise conventional amino acid solution and/or glutamine or analogues thereof, L-asparagine and/or acetoacetate. The invention also relates to a composition comprising conventional amino acid mixture and alpha-ketoglutarate or analogues thereof, in such an amount, so that it provides more than 0.25 g/kg body weight/day of alpha-ketoglutarate, when administered to the patient, optionally with the addition of glutamine or analogues thereof, L-asparagine and/or acetoacetate, glucose and/or fat.

7 Claims, No Drawings

USE OF ALPHA-KETOGLUTARATE

This application is a continuation of Ser. No. 08/175,403, filed as PCT/SE93/00426, May 14, 1993 published as WO93/23027, Nov. 25, 1993, now abandoned.

The present application relates to the use of alpha-ketoglutarate in the preparation of a medicament for treatment of critically ill patients for improving protein synthesis capacity and preserving the lean body mass and for improving the glutamine content and maintaining energy status in skeletal muscle, especially of a medicament containing alpha-ketoglutarate in such an amount, so that it provides more than 0.25 g/kg body weight/day of alpha-ketoglutarate, when administered to the patient.

It also relates to a composition containing conventional amino acid mixture and alpha-ketoglutarate in such an amount, so that it provides more than 17,5 g/day, (17,5 g/L) of alpha-ketoglutarate, optionally with the addition of glutamine or analogues thereof, glucose and/or fat.

The glutamine content in skeletal muscle of critically ill patients who are treated with TPN (Total Parenteral Nutrition) according to common method of today is not influenced by this conventional treatment. Also when glutamine is given additionally in an amount of 20 g/day per person, only a moderate influence on the skeletal muscle glutamine of critically ill patients could be established.

It must be regarded as surprising that the use of alpha-ketoglutarate has an influence on the glutamine content in skeletal muscle of critically ill patients.

BACKGROUND OF THE INVENTION

In states of illness, surgical operations and injuries, profound changes are induced in the energy and protein metabolism of the human body. This means, for example, loss of active cellular mass, leading to muscular fatigue, pronounced apathy and loss of appetite, and a period of convalescence involving general weakness which, for instance after a biliary tract operation, may last 5–6 weeks before the patient has regained his normal function. The cellular mass which is broken down very rapidly in different states of illness will need a time for re-establishment which is about four times as long as the time of breakdown for the same mass.

In critical states of illness and injuries, parenteral nutritional support is generally applied. In the past, preparations for intravenous nutritutional support generally contained an aqueous solution of a high caloric content carbohydrate, such as glucose and the like, fat and electrolytes. In prolonged states of illness or in injuries the nitrogen balance of the body must however be considered, i.e. the ratio of nitrogen loss to nitrogen intake. In the case of negative nitrogen balance, the parenteral nutritional support can be supplemented with amino acid supply to improve the nitrogen balance. Different amino acid compositions for parenteral supply are previously known, see e.g. SE Patent Application 8203965-2 and DE-A 25 30 246 concerning amino acid nutrient compositions in renal failure, WO 82/00411 concerning a nutrient composition containing branched-chain amino acids, and WO 83103969 concerning an aqueous nutrient solution consisting of L-amino acids.

From a survey made of the free amino acid pattern in the muscles, it has been found that skeletal muscle, which is the major body tissue in respect of weight, has a free amino acid pool, 62% of which consists of glutamine, see Bergström et al: Intracellular free amino acid concentration in human muscle tissue, J. of Appl. Physiol., Vol 36, No 6, 1874. In states of illness, injuries or surgical operations, this content decreases by 40–50%, see Vinnars et al: Influence of the postoperative state on the intracellular free amino acids in human muscle tissue. Annals of Surg., Vol 182, 6:665–671, 1975 and in states of blood poisoning, even more,.

It has been found that this glutamine reduction cannot be affected by enteral or parenteral nutritional support according to the methods hitherto available, see Vinnars et al: Metabolic effects of four intravenous nutritional regiments in patients undergoing elective surgery. II. Muscle amino acids and energy rich phosphates. Clin. Nutr. 2:3–11, 1983. There probably is a correlation between the inability immediately postoperatively to make a negative nitrogen balance positive and to normalise the exhausted intracellular glutamine pool and the reduced muscular mass and strength. This reduction probably depends on a reduced protein synthesis capacity post traumatically in skeletal muscle, see Werneman et al: Protein synthesis after trauma as studied by muscle ribosome profiles. Proceedings in the 7th ESPEN Congress. Ed. Dietze et al, Karger, Basel.

The addition to the nutritional support of a dipeptide of the type ornithine-alpha-ketogtutarate to a commercial amino acid solution has been found to improve to some extent, whereas not to normalise the intracellular glutamine pool, see Leander et al: Nitrogen sparing effect of Ornicetil in the immediate postoperative state. Clin. Nutr. 4:43–51, 1985. This preparation is however very expensive, and it has not been possible so far to evaluate whether its use in parenteral nutrition confers a clinical advantage.

When a patient is critically ill, it becomes necessary to resort to intravenous feeding. The nutrition substrates available for energy metabolism are various sugar solutions and fatty emulsions, which today seem appropriate. However, the amino acid solutions commercial available are inadequate, because they lack or have too low concentration of important amino acids such as tyrosine, cysteine, asparagine or glutamine. This is due to difficulties in heat-sterilising solutions of the amides, and also to the fact that the amides are unstable when stored. Another problem is that some of these compounds are relatively sparingly soluble and therefore require large amounts of water when being prepared.

After elective surgery, for instance biliary tract operations, it has been found that the negative nitrogen balance primarily depends on reduced protein synthesis which is assessed by determining the ribosome activity in skeletal muscle, see Werneman et al: Protein synthesis in skeletal muscle after abdominal surgery: The effect of total parenteral nutrition. JPEN, 1985. An increased protein breakdown occurs only in very critical traumas and primarily in septic states. This reduced protein synthesis capacity cannot be affected by conventional intravenous or enteral nutritional support.

WO 89/03688 discloses that alpha-ketoglutarate has the same effect as glutamine when given to postoperative patients. Preliminary tests on patients subjected to a biliary tract operation showed that an addition of alpha-ketoglutarate to a conventional parenteral nutritional support program improves the nitrogen balance of the patients. Besides, the pathological amino acid changes which normally occur after injury or surgical operation are normalised and, also, the reduction of the ribosome activity is prevented.

Critically ill patients is a group of patients who are very ill. They have one or multiple organ failure, such as respiratory problem, renal, liver and/or intestinal insufficiency, a general protein catabolism and must be under intensive care.

This group is different from the group of postoperative patients, who often has normal glutamine and protein values before the operation and for who the drop in glutamine level is due to the operation. Critically ill patients have a pronounced protein catabolism and a lower skeletal glutamine content than postoperative patients.

Critically ill patients have a decrease of at least 50% of the normal glutamine concentration in skeletal muscle. In extreme cases there is a drop to 70–80%. Roth et al (Clin Nutr 1:25–42, 1982) have shown that there is correlation of mortality of the patients with a decrease of more than 70%.

Jeppson et al (Am J Physiol 1988, 255, E166–172) has shown a correlation between the protein synthesis and glutamine level in skeletal muscle. By improving the glutamine level in skeletal muscle the protein synthesis capacity is improved and the lean body mass is preserved. This correlation is of importance for the interpretation of the results given in the example below.

Earlier studies (J. Karner and E. Roth, Clin Nutr. Vol 9, 1990, 43–44) have shown that when alanylo-glutamine is given in an amount of 20 g/day per patient to two patients, no influence on the skeletal muscle of critically ill patients could be established and when 40 g/day per patient was given to two patients, a marginal improvement of the muscle glutamine concentration could be seen. When 60 g/day was given to two patients an improvement of 50–100% was found.

It is also of importance to maintain the energy status in the skeletal muscle tissue for critical ill patients. The energy status is coupled to the protein synthesis, but the mechanism is not totally known.

THE INVENTION

It has now been demonstrated for the first time that the addition of alpha-ketoglutarate, alone or in combination with conventional amino acid solutions to a parenteral nutrition program can improve the reduction of the protein synthesis capacity for critically ill patients, maintain energy status in the skeletal muscle tissue and also improve the muscle glutamine concentration with almost 100%.

A larger effect has been obtained compared to glutamine given in equal amount (J. Karner and E. Roth). This must be regarded as surprising. The abnormal amino acid pattern intracellularly in skeletal muscle for critically ill patients, and especially the 50% reduction of the glutamine pool involved, can then, by the addition of alpha-ketoglutarate, be partially normalised.

The present invention relates to the use of alpha-ketoglutarate or analogues thereof in the preparation of a medicament for treatment of critically ill patients for improving protein synthesis capacity, maintaining energy level and preserving the lean body mass and for improving the glutamine content, especially in such an amount so that it provides more than 0.25 g/kg body weight (bw)/day of alpha-ketoglutarate when administered to the patient. The medicament can also comprise conventional amino acid solution and/or glutamine or analogues thereof, L-asparagine and/or acetoacetate.

By analogues is meant e.g. salts, esters and dipeptides.

The present invention also relates to a method for treatment of critically ill patients for improving the glutamine content in skeletal muscle and thereby improving protein synthesis capacity, maintaining energy level and preserving the lean body mass comprising administration of alpha-ketoglutarate or an analogue thereof.

Alpha-ketoglutarate may be given alone or in combination with a conventional amino acid solution, optionally with the addition of L-glutamine or analogues thereof, L-asparagine and/or acetoacetate, glucose and/or fat.

The invention also refers to a composition for treatment of critically ill patients for improving protein synthesis capacity, Maintaining energy level, preserving the lean body mass and for improving the glutamine contentin skeletal muscle comprising conventional amino acid mixture and alpha-ketoglutarate or analogues thereof, in such an amount, so that it provides more than 0.25 g/kg body Weight/day of alpha-ketoglutarate, when administered to the patient. i.e. 17,5 g/day for a person of 70 kg, optionally with the addition of glutamine or analogues thereof, L-asparagine and/or acetoacetate. Glucose and/or fat can also be added.

Preferably the composition contains alpha-ketoglutarate in a higher amount than 17,5 g/L, or more preferably in a higher amount than 25 g/L.

An upper limit of the dose of alpha-ketoglutarate is related to the tolerated level for the patient. No investigations have been done, but an upper limit could be estimated to be about 80–100 g/day per patient.

The use of alpha-ketoglutarate is not limited to parenteral administration but can also be administered orally. The suggested doses for alpha-ketoglutarate is applicable both for parenteral and oral administration.

The conventional amino acid solution is given parenterally.

By critically ill patients is meant a group of patients who have one or multiple organ failure, and a general protein catabolism. They are treated in intensive care units, often under mechanical ventilation and/or dialysis.

The amount of alpha-ketoglutarate is here calculated on the need of the patient per day (i.e. 24 hours). It is the only proper way of defining the amount, as the amount always must depend on body weight (bw) of the patient and the time period for the amount. Normally the alpha-ketoglutarate or its analogue is given together with the solution comprising conventional amino acids. The amount for such a solution is often about one liter per day, but this very much depending on concentration of the solution and the amount of liquid that can be given to the patient.

All scientific report regarding amino acid administration and supplement thereto are calculating the amount in g per body weight and time or in g N per body weight and time. This is the only proper way for a doctor to decide the amount for the patient.

When giving the alpha-ketoglutarate parenterally together with amino acid solution and other additives, the products can either be heat sterilised or brought into a form suitable for administration by sterile filtration of an aqueous solution, followed by rapid cooling and cold storage limited to a few months. One alternative is freeze-drying of the sterile-filtered solution, yielding a sterile powder. Immediately before administration, this powder can be added to a conventional amino acid mixture. Also other forms of powder sterilisation, not relying on heat, are conceivable. The possibility of using the sodium salt or esters of the compounds in order to increase the solubility has also been considered.

The concentration of at least 0.25 g/kg body weight/day corresponds to at least 17,5 g component/L aqueous solution if 1 L amino acid solution/day is given to a patient weighing 70 kg. One example of a conventional amino acid solution expressed in g dry component/L aqueous solution is:

| | |
|---|---|
| glycine | 1-12 |
| aspartate | 1-10 |
| glutamate | 2-12 |
| alanine | 2-20 |
| arginine | 2-14 |
| cysteine/cystine | 0.4-2.0 |
| histidine | 2-8 |
| isoleucine | 2-8 |
| leucine | 2-8 |
| lysine | 2-12 |
| methionine | 1-6 |
| phenylalanine | 4-10 |
| proline | 4-10 |
| serine | 2-10 |
| threonine | 2-8 |
| tryptophan | 1-3 |
| tyrosine | 0.2-1 |
| valine | 2-8 | and optionally 5-30 g/l L-glutamine or analogues thereof and/or 0.5-10 g/l L-asparagine and/or 0.5-10 g/l acetoacetate, or salts or esters thereof.

The added amount of L-glutamine to be given together with this amino solution is at least 17,5 g/L and an especially preferred amount is more than 25 g/L When sparingly soluble amino acids are given as dipeptides, the amounts given above for e.g. glutamine, cysteine and tyrosine, can be higher.

Preferred compositions could include the following suitable components (expressed in g dry component/l aqueous solution):

| Amino acid solution | 1 | 2 | 3 | 4 | 5 |
|---|---|---|---|---|---|
| glycine | 5.9 | 5.9 | 5.9 | 5.9 | 5.9 |
| aspartate | 4.8 | 4.8 | 4.8 | 4.8 | 4.8 |
| glutamate | 6.8 | 6.8 | 6.8 | 6.8 | 6.8 |
| alanine | 12.0 | 12.0 | 12.0 | 12.0 | 12.0 |
| arginine | 8.4 | 8.4 | 8.4 | 8.4 | 8.4 |
| cysteine/cystine | 0.42 | 0.42 | 0.42 | 0.42 | 0.42 |
| histidine | 5.1 | 5.1 | 5.1 | 5.1 | 5.1 |
| isoleusine | 4.2 | 4.2 | 4.2 | 4.2 | 4.2 |
| leucine | 5.9 | 5.9 | 5.9 | 5.9 | 5.9 |
| lysine | 6.8 | 6.8 | 6.8 | 6.8 | 6.8 |
| methionine | 4.2 | 4.2 | 4.2 | 4.2 | 4.2 |
| phenylalanine | 5.9 | 5.9 | 5.9 | 5.9 | 5.9 |
| proline | 8.0 | 8.0 | 8.0 | 8.0 | 8.0 |
| serine | 6.0 | 6.0 | 6.0 | 6.0 | 6.0 |
| threonine | 4.2 | 4.2 | 4.2 | 4.2 | 4.2 |
| tryptophan | 1.4 | 1.4 | 1.4 | 1.4 | 1.4 |
| tyrosine | 0.4 | 0.4 | 0.4 | 0.4 | 0.4 |
| valine | 5.5 | 5.5 | 5.5 | 5.5 | 5.5 |
| asparagine | — | — | — | 2.0 | 4.0 |
| acetoacetate | — | — | — | 2.0 | — | alpha-ketoglutarate should then be added to these solutions in an amount of more than 17,5 g/L, preferably 25 g/L or more.

When alpha-ketoglutarate is included in the composition, it must be added in the form of its sodium salt or its esters, since it is otherwise extremely sparingly soluble and unstable. Glutamine can also be added in the form of the sodium salt thereof, thus improving its solubility.

Implementation of the invention

When preparing a composition including alpha-ketoglutarate, heat sterilization can be used if the components are not heat sensitive. When including heat sensitive components, such as L-glutamine, they can be dissolved in sterile pyrogen-free water at 30°-50° C. The solution is sterile-filtered and rapidly cooled and may thereafter be stored for a few months in a solution in a cooled state or for an even longer time in the frozen state, or stored after freeze-drying for several years in sterile powder form, until it should be used together with an amino acid solution of conventional commercial type, for instance of the Vamin® type (amino acid nutrient composition from Kabi Pharmacia AB). Carbohydrates and fatty substances can also be added to the infusion solution. When using alpha-ketoglutarate, this must be added in the form of its sodium salt or its esters, which is also possible, but not necessary, in the case of L-glutamine.

A new prepared composition as above, either in large bags or in separate vials for each substrate, is then administrated to patients exhibiting disordered nitrogen balance with a critical illness The administration being conducted during a period of from 2-4 days to several weeks e.g. with an addition of nutrition to reach a dosage of 120-170 kJ/kg body weight/day, including 0.1-0.2 g amino acid nitrogen/kg body weight/day.

By improving glutamine concentration in skeletal muscle and maintaining the energy level, a critically ill patient can be faster mobilised with less complications and thereby the patient need a shorter time for convalescence.

The treatment with alpha-ketoglutarate reduces a lowering of glutamine level in skeletal muscle.

By preserving the lean body mass of the patients they are less susceptible for complications during illness and can recover faster from convalescence.

EXAMPLE 1

19 patients in acutely critical catabolic conditions with low muscle glutamine level were studied.

During five to six days a TPN program was given. The energy (70-130 kJ/bw/day) was given as equal amounts of glucose and fat together with amino acids (0.1-0.2 gN/kg bw/day). 13 patients served as controls (Group A) and 6 patients (Group B) were given an addition of 0.28 g/kg bw/day alpha-ketoglutarate (AKG). Percutaneous muscle samples were taken from the quadriceps femoris muscle before and after TPN treatment. The concentrations of amino acids were determined by ion exchange chromatography and expressed as mmol/kg wet weight (ww) muscle. Results. In both groups low glutamine levels were noted prior to TPN treatment, 3.00±0.46 and 3.04±0.34 mmol/kg ww (wet weight) muscle in the control- and AKG-groups respectively. These values should be compared with 12.61±0.54 observed in otherwise healthy patients undergoing elective abdominal surgery. In the control the values remained unchanged throughout the study period (2.98±0.36 mmol/kg ww), whereas the glutamine concentration increased to 5.18±1.10 mmol/kg ww ($P<0.05$) in the AKG-group.

TABLE 1

| | Group A control | Group B AKG |
|---|---|---|
| AKG, g/kg bw/day glutamine level mmol/kg | — | 0.28 |
| Prior treatment | 3.00 ± 0.46 | 3.04 ± 0.34 |
| After treatment | 2.98 ± 0.36 | 5.18 ± 1.10 |

Conclusion. The very low glutamine values in critically ill intensive care patients are possible to increase by AKG supplementation. This indicates that the skeletal muscle is the target organ for the AKG treatment and moreover and evidence for the metabolisation of AKG to glutamine in skeletal muscle tissue.

EXAMPLE 2

12 critically ill patients on mechanical ventilation under intensive care were studied during five days whilst given TPN including 95–125 kcal/24 hours and 0.1–0.15 g N 24 hours adjusted to the basal energy expenditure. The patients were randomised to receive supplementation with glutamine (gln), 0.28 g/kg bw/24 h or 0.28 AKG g/kg bw/24 h, in which case the conventional nutrition was reduced in order to obtain an isocaloric and isonitrogenous support between the groups. Percutaneous muscle biosies were taken before and after the study period from the lateral portion of the quadriceps femoris muscle. The muscle specimens were analysed for their content of DNA, RNA (Munro & Fleck), alkali soluble protein (ASP) (Lowry) and ATP, creatine (Cr) and phosphocreatine (PCr) (Hultman). Cr and PCr indicates the energy status in the cell.

Result. The content of DNA, RNA and ASP in muscle was unaltered during the study period although the levels were low as compared to healthy controls. The levels of ATP were $20.5\pm1.3$ mmol/kg fat-free solid (FFS) for the control group, $22.0\pm1.6$ for the glutamine group (Gln) and $19.1\pm0.8$ for the AKG group respectively. This level did not change significantly during the treatment period. The creatine (Cr) and phosphocreatine (PCr) contents are given in Table 2.

TABLE 2

|  |  | Controls | Gln | AKG |
|---|---|---|---|---|
| PCr mmol/kg | Day 0 | $77.0 \pm 4.4$ | $82.1 \pm 11.1$ | $60.2 \pm 6.7$ |
| FFS | Day 5 | $67.1 \pm 5.1$ | $75.5 \pm 6.7$ | $66.3 \pm 13.2$ |
| Cr mmol/kg | Day 0 | $71.1 \pm 12.9$ | $66.5 \pm 6.9$ | $75.0 \pm 1.7$ |
| FFS | Day 5 | $71.1 \pm 12.3$ | $71.2 \pm 7.7$ | $83.3 \pm 6.2^*$ |

*significant

Conclusion. TPN supplemented with glutamine or AGK does not alter the content of protein or RNA in muscle of critically ill patients during 5 days of treatment. However, supplementation with AKG improves significantly the energy status of the tissue in terms of maintained levels of ATP and PCr in parallel with an elevation of the free creatine level. This finding is a very important and surprising finding, which can have a great impact for treatment of critically ill patients.

We claim:

1. A method for treating critically ill patients suffering from one or multiple organ failure or sepsis and a general protein catabolism having more than a 50% reduction of the intracellular glutamine level in skeletal muscles and under intensive care the improvement comprising the step of administering alpha-ketoglutarate, in order to improve the protein synthesis capacity, maintaining the energy level and to preserve the lean body mass, wherein more than 0.25 g/kg body weight/day of alpha-ketoglutarate is administered to the patient.

2. The method of claim 1, wherein a composition providing more than 17.5 g/day of alpha-ketoglutarate is administered.

3. The method of claim 2 wherein the administered composition in addition to alpha-ketoglutarate comprises at least one member selected from the group consisting of glutamine, L-asparagine, acetoacetate, glucose and fat.

4. The method of claim 3 wherein the composition further comprises a conventional amino acid mixture.

5. The method of claim 2 wherein the composition further comprises a conventional amino acid mixture.

6. The method of claim 1 wherein said patients have a 70–80% reduction of said intracellular glutamine.

7. Composition for treatment of critically ill patients having one or more organ failures or sepsis and a general catabolism which have more than a 50% reduction of the glutamine level in skeletal muscles and under intensive care, in order to improve protein synthesis capacity, maintaining energy level, preserving the lean body mass, consisting essentially of a conventional amino acid mixture and more than 25 gl of alpha-ketoglutarate or admixtures of these with at least one member selected from the group consisting of glutamine, L-asparagine, acetoacetate, glucose and fat.

* * * * *

UNITED STATES PATENT AND TRADEMARK OFFICE
CERTIFICATE OF CORRECTION

PATENT NO. : 5,646,187
DATED      : July 8, 1997
INVENTOR(S) : Vinnars, et. al.

It is certified that error appears in the above-indentified patent and that said Letters Patent is hereby corrected as shown below:

Title page, item [73], Assignee:   should read--AB Erik Vinnars of Stockholm, Sweden--.

Signed and Sealed this

Twenty-first Day of October 1997

Attest:

BRUCE LEHMAN

*Attesting Officer*    *Commissioner of Patents and Trademarks*